United States Patent
Miller et al.

(10) Patent No.: US 7,429,621 B2
(45) Date of Patent: Sep. 30, 2008

(54) CYCLONE REACTOR AND ASSOCIATED METHODS

(75) Inventors: Jan D. Miller, Salt Lake City, UT (US); Jan Hupka, Salt Lake City, UT (US); Wlodzimierz W. Zmierczak, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 10/592,606

(22) PCT Filed: Mar. 11, 2005

(86) PCT No.: PCT/US2005/008316

§ 371 (c)(1), (2), (4) Date: Jul. 6, 2007

(87) PCT Pub. No.: WO2005/090272

PCT Pub. Date: Sep. 29, 2005

(65) Prior Publication Data

US 2007/0249737 A1    Oct. 25, 2007

Related U.S. Application Data

(60) Provisional application No. 60/552,894, filed on Mar. 12, 2004, provisional application No. 60/589,971, filed on Aug. 3, 2004.

(51) Int. Cl.
    *C07C 27/00* (2006.01)
    *C01B 3/26* (2006.01)

(52) U.S. Cl. .................. 518/700; 518/701; 518/702; 518/703; 423/651; 252/373

(58) Field of Classification Search ......... 518/700–703; 423/651; 252/373
    See application file for complete search history.

(56) References Cited

U.S. PATENT DOCUMENTS

| | | |
|---|---|---|
| 4,279,743 A | 7/1981 | Miller |
| 4,397,741 A | 8/1983 | Miller |
| 4,399,027 A | 8/1983 | Miller |
| 4,705,908 A | 11/1987 | Gondouin |
| 4,744,890 A | 5/1988 | Miller et al. |
| 4,818,295 A | 4/1989 | Converse et al. |
| 4,838,434 A | 6/1989 | Miller et al. |
| 4,881,476 A | 11/1989 | Becker et al. |
| 5,472,567 A | 12/1995 | Torregrossa |
| 5,529,701 A | 6/1996 | Grisham et al. |
| 5,730,875 A | 3/1998 | Grisham et al. |
| 6,830,608 B1 | 12/2004 | Peters |
| 6,918,949 B1 | 7/2005 | Peters |
| 2003/0146523 A1 | 8/2003 | Morse et al. |

FOREIGN PATENT DOCUMENTS

| | | |
|---|---|---|
| EP | 0473566 | 3/1992 |
| EP | 0 478 528 | 4/1992 |

*Primary Examiner*—Jafar Parsa
(74) *Attorney, Agent, or Firm*—Thorpe North & Western LLP

(57) ABSTRACT

A method of synthesizing and reacting compounds in a cyclone reactor (10) is disclosed and described. A liquid carrier can be provided which can include solid catalyst particles, liquid catalysts, and/or liquid reactants. The liquid carrier can be formed into a swirl layer (38) within the cyclone reactor (10). A reactant composition including at least one reactant can also be injected through at least a portion of the swirl layer (38) such that at least a portion of the reactant is converted to a reaction product. The cyclone reactor (10) allows for improved contact of reactants and catalyst, with fine temperature control, thus increasing reaction yields and selectivity

22 Claims, 1 Drawing Sheet

CYCLONE REACTOR AND ASSOCIATED METHODS

FIELD OF THE INVENTION

The present invention relates generally to devices and methods for synthesizing chemical compounds. Accordingly, the present invention involves the fields of chemistry, reactor design, materials science, and physics.

BACKGROUND OF THE INVENTION

Due to the inherent societal difficulties of using nuclear and most alternative energies, there is a great need to identify and develop new and suitable forms for energy storage and distribution. Hydrogen and/or some synthesis gas products, e.g., methanol, dimethyl ether, synthetic diesel fuel, etc., may very well one day replace most of the existing energy carriers. The economy of production of such products and chemicals depends greatly on the efficiency of reactors used for their synthesis.

Therefore, devices and methods which improve selectivity and/or yields of a wide variety of synthesis processes would be a significant advancement in the area of reactor design and chemical synthesis.

SUMMARY OF THE INVENTION

In accordance with the present invention, a method of synthesizing compounds can include providing a liquid carrier in a swirl layer. A reactant composition including at least one reactant can be injected through at least a portion of the swirl layer such that at least a portion of the reactant is converted to a synthesized compound. In one aspect, the swirl layer can be formed by tangential injection of the liquid carrier into a reactor.

Although a number of reactors can be used, the currently preferred configuration is a gas or liquid-sparged cyclone. FIG. 1 shows a gas-sparged cyclone reactor which is described in more detail below. In a gas-sparged cyclone reactor the gas composition can be forced through a porous material configured to sparge and increase the surface area of the gas composition. Advantageously, the flowrate of the liquid carrier can be easily adjusted to achieve a predetermined film thickness of the swirl layer and residence time of reactants.

As the swirl layer travels downwardly through the vertical reactor, synthesized compounds and/or reaction products can be removed from the reactor. Typically, the swirl layer rotates in an annular or cylindrical film surrounding a center gaseous-froth core, although this is not required. Therefore, in one aspect, the froth core and swirl layer can be removed separately from the reactor, thus reducing the need for additional separation steps. The froth core can be removed from either the top or bottom of the reactor. Depending on the particular components in each outlet stream, additional separations can include a gas-liquid separator or liquid-liquid separation process.

In one additional aspect of the present invention, the swirl layer creates a vortex induced pressure differential sufficient to increase transfer of gaseous reactants through the swirl layer. The swirl layer can have a thickness from about 5% to about 20% of a diameter of the reactor, and preferably about 10%. Thus, throughput per reactor volume can be increased because of improved contact and increased heat and mass transfer. Further, the devices and methods of the present invention can suppress side-reactions and increase selectivity.

Finally, an additional benefit of the design is a gas cushion at the porous tube surface which reduces erosion of internal surfaces due to contact with the catalyst mixture.

Typical synthesis reactions are exothermic, thus heat can be removed from the swirl layer via any number of cooling elements. For example, cooling coils or other cooling elements can be placed within the swirl layer, preferably with minimal flow disturbance. Optionally, an external jacket or cooling tubes can be placed in thermal contact with the reactor body.

The devices and methods of the present invention can be used in a wide variety of chemical reactions. By way of example, the chemical reaction can be a catalytic reaction. As such, a solid catalyst material can be provided as part of the liquid carrier to form a solid-liquid catalyst slurry. Alternatively, the catalyst material can be provided as a liquid catalyst, or a catalyst which is soluble in the carrier, which is mixed with the liquid carrier. Optionally, or in addition to a catalyst mixture or slurry, a catalyst material can be part of the porous layer through which the gas composition is forced. The catalyst material can be coated on the porous layer or held between two porous layers. Such catalytic reactions are multi-phase reactions including a solid or liquid catalyst, liquid carrier, a gas reactant, and optionally, reaction products. In some embodiments, the catalytic reactions are reactions involving at least three-phases. Depending on the physical state of the reactants, the liquid carrier and/or gas composition can include at least one reactant.

In another alternative aspect of the present invention, the catalyst mixture can be directly recycled to the reactor without treatment. However, depending on the specific synthesis reaction, some separation and/or catalyst treatment may be necessary.

Any suitable liquid can be used as the liquid carrier. The liquid carrier can be inert with respect to the reaction or can be a reactant. Several non-limiting examples of suitable liquid carriers include mineral oils such as paraffin oils, heavy fractions of the product, water, liquid reactant, liquid catalyst, and mixtures of these materials. Those skilled in the art can choose suitable liquid carriers based on the desired chemical reaction, viscosities, operating temperature, potential reactions with reactants or other species, ease of separation, and the like. Thus, although heavier oils are commonly preferred, in some cases lower molecular weight liquids may be suitable, e.g., lower hydrocarbons with a carbon number of less than twelve.

In still another aspect of the present invention, the reactant composition can depend on the specific synthesis reaction desired. Either gas or liquid compositions can be used which contain specific reactants. Several specific reactions are described in more detail below. However, in some embodiments, the reactant composition can include hydrogen and carbon monoxide, oxygen alone, oxygen and gaseous reactant, hydrogen alone, or gaseous reactant alone.

A wide range of chemical synthesis processes can be carried out using the devices and methods of the present invention. Several examples of classes of reactions which are suitable for use in the present invention include, but are not limited to synthesis of methanol, dimethyl ether, Fischer-Tropsch products, higher alcohols, oxidation products, alkylation products, oligomerization products, hydrogenation products, and hydrotreated hydrocarbons. Several of these types of reactions are described in more detail below.

There has thus been outlined various features of the invention so that the detailed description thereof that follows may be better understood, and so that the present contribution to the art may be better appreciated. Other features and advantages of the present invention will be apparent from the following detailed description of the invention and corresponding drawings, taken with the accompanying claims, or may be learned by the practice of the invention.

Figures 1, 2:
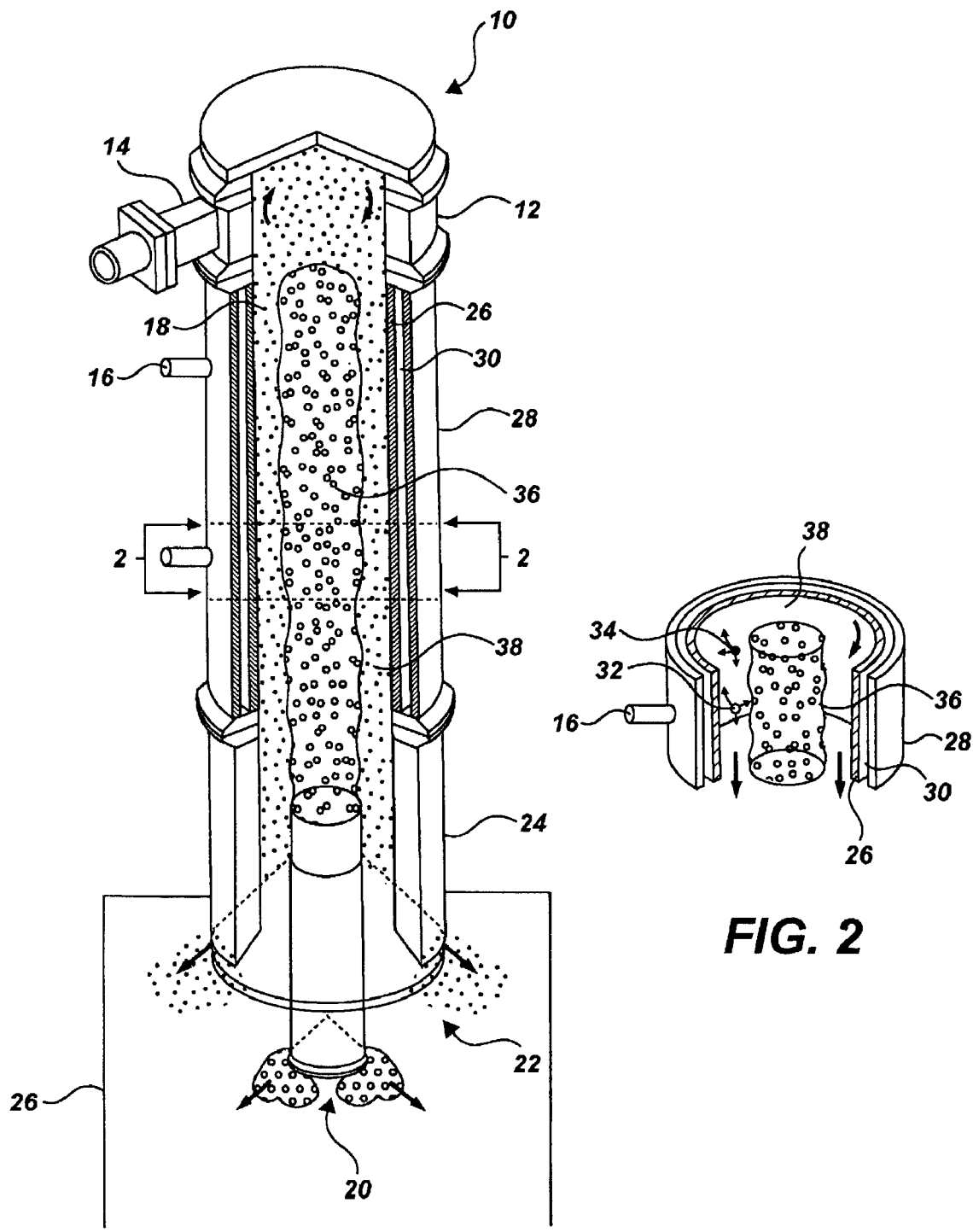
FIG. 1 is a cut-away perspective view of a catalytic gas-sparged cyclone reactor in accordance with one embodiment of the present invention.
FIG. 2 is a cut-away perspective view of a cross-section of the cyclone reactor of FIG. 1.

The figures are provided for illustrative purposes only and are not necessarily drafted to scale. As such, variations can be had as to dimensions and proportions illustrated without departing from the scope of the present invention.

DETAILED DESCRIPTION

Reference will now be made to the exemplary embodiments illustrated in the drawing, and specific language will be used herein to describe the same. It will nevertheless be understood that no limitation of the scope of the invention is thereby intended. Alterations and further modifications of the inventive features, process steps, and materials illustrated herein, and additional applications of the principles of the inventions as illustrated herein, which would occur to one skilled in the relevant art and having possession of this disclosure, are to be considered within the scope of the invention. It should also be understood that terminology employed herein is used for the purpose of describing particular embodiments only and is not intended to be limiting.

A. Definitions

In describing and claiming the present invention, the following terminology will be used.

The singular forms "a," "an," and "the" include plural referents unless the context clearly dictates otherwise. Thus, for example, reference to "an inlet" includes reference to one or more of such inlets.

As used herein, "swirl layer" refers to a volume of liquid carrier which has a circular or swirl flow pattern. In some cases, the swirl layer can be viewed as a rotating film of liquid such that any given particle within the liquid carrier follows a generally spiral path along the reactor toward the outlet. Those skilled in the art will recognize that fluid flow patterns can include turbulent mixing and can vary significantly. Further, gradients in flow velocity can vary radially as well as along the length of the reactor.

As used herein, "substantially free of" or the like refers to the lack of an identified element or agent in a composition. Particularly, elements that are identified as being "substantially free of" are either completely absent from the composition, or are included only in amounts which are small enough so as to have no measurable effect on the composition.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

B. The Invention

Reference will now be made to the drawing in which the various elements of the present invention will be discussed. It is to be understood that the following description is only exemplary of the principles of the present invention, and should not be viewed as narrowing the appended claims.

The manufacturing economy of catalytic conversion products is highly dependent on the efficiency of reactors used during synthesis processes. In one embodiment of the present invention, a slurry gas-sparged cyclone reactor (SG-SCR) for multi-phase (gas, liquids and/or solids containing) catalytic processes can provide a reaction environment which allows for improved selectivity, improved yield and high reliability. Alternatively, the present invention can be operated as a liquid-sparged cyclone reactor.

Referring now to FIG. 1, a cyclone reactor 10 can be used to establish a controlled high force field by swirl flow in order to increase the inertia of fine catalyst particles suspended in the slurry and to produce a high density of very small gas reactant bubbles with directed motion in order to improve collision efficiency. The cyclone reactor can include a reactor body which can be comprised of multiple sections, although a single unit could be manufactured. In the embodiment shown in FIG. 1, a header unit 12 can have an inlet 14 operatively connected to the header. The header unit and inlet can be configured to produce vortex flow of the catalytic mixture within the reactor body. In one aspect, the vortex flow can be produced by an offset inlet flow.

One or more secondary inlets 16 can be operatively connected to the reactor body. As described in more detail below, the secondary inlets can be configured for use in introducing either solid, gas, and/or liquid reactants into the interior chamber 18 of the cyclone reactor 10. An alternative gas underflow outlet 20 can be operatively connected to a discharge unit 24 portion of the reactor body to remove gas and froth phases from the cyclone reactor. Additionally, a liquid underflow outlet 22 can be operatively connected to the discharge unit to remove liquid phases from the cyclone reactor. Thus, the cyclone reactor can be a flow-through reactor such that materials enter one portion of the interior chamber and exit a separate portion of the interior chamber.

In the embodiment shown in FIG. 1, the liquid underflow outlet 22 is concentrically oriented around the gas underflow outlet 20. However, this is not required. For example, the entire underflow of the cyclone reactor can be directed to a separate unit for further reaction and/or separations. Thus, in some embodiments, a separator 26 can be operatively connected to the discharge unit 24. Non-limiting examples of such separators can include gas-liquid separators, liquid-liquid separators, or the like. Such separators are well-known to those skilled in the art and can be chosen based on the particular reaction products.

In one embodiment, the SG-SCR can combine basic features of both the air-sparged hydrocyclone as described in U.S. Pat. No. 4,279,743, which is incorporated herein by reference in its entirety, and a typical slurry reactor. In another aspect, the present invention can be used as a catalytic multiphase reactor. Further, although the figure illustrates a vertical reactor, the actual orientation can be varied to almost any position. Typically, the liquid carrier, swirl layer and gases travel at a sufficiently high velocity to make the direction of gravity largely irrelevant. Therefore, in some embodiments, the reactor can be oriented in a horizontal position.

Description of SG/L-SCR

Referring again to FIG. 1, the cyclone reactor 10 is shown wherein a liquid carrier can be fed tangentially through a cyclone header 12 into the interior chamber 18 to develop a swirl flow of a certain thickness in the radial direction. The liquid carrier can include a liquid and/or solid catalyst material. For example, solid catalyst particles can be suspended in the liquid carrier, e.g., an oil, to form a catalyst slurry. Alternatively, a liquid catalyst can be mixed in the liquid carrier to form a catalyst mixture. In an additional optional embodiment, the liquid carrier can comprise, or consist essentially of, a liquid reactant.

In another optional embodiment, the cyclone reactor can include a separate mixer to maintain a swirl flow of the liquid carrier. Preferably, the swirl flow of the liquid carrier forms a rotating layer or film of the liquid carrier.

Typically, a gas sparging device can be placed between the gas inlet 16 and the interior chamber 18 of the cyclone reactor body. The gas sparging device can be any device capable of increasing surface area of the gas for contact with the liquid. Specific non-limiting examples of suitable gas sparging devices include porous tubes, mesh, grating, asymmetric static mixers, and the like. Porous tubes can be produced of metal (e.g. stainless steel), INCONEL (Ni—Cr—Fe alloys), ceramic and plastic frits as well as stainless steel mesh or perforated tubes. In one embodiment, the gas sparging device can be a porous catalyst layer oriented at the gas inlet such that the gas composition passes substantially through the porous catalyst layer into the reactor body. In an additional embodiment, the reactor body can include a gas plenum adjacent at least a portion of the cyclone body.

Gas reactants can be sparged through the gas sparging device such as the jacketed porous tube wall 26 shown in FIG. 1. Further, the porous tube wall can be placed concentrically within the reactor outer shell 28 such that an open space 30 is therebetween. As the gas flows through the porous wall it is sheared into numerous small bubbles by the high velocity swirl flow of the liquid carrier. As shown in FIG. 2, bubbles 32 accelerating toward the inner surface of the swirl layer collide with catalyst particles 34, and undergo catalytic reaction in the presence of the liquid. As noted herein, a pressure differential tends to draw the bubbles towards the center to form the froth core 36, while the catalyst particles tend to be retained in the swirl layer 38.

Referring again to FIG. 1, the liquid carrier, and gas/froth core containing unreacted gas and low boiling point components can be discharged as an underflow product through the discharge unit 24. The rate of discharge from the reactor can be adjusted by liquid carrier and gas/froth discharge valves to control pressure and retention time as desired. Further, the rates of inflow at each of the inlet 14 and the secondary inlet 16 can be adjusted to control the outlet rates and swirl properties to achieve desired retention times.

Alternatively, the cyclone reactor can be operated as a liquid sparged cyclone reactor (SL-SCR). In this case, the reactants can be provided as a liquid which is then sparged as it enters the cyclone reactor in a similar manner. Although the descriptions herein focus primarily on gas-sparged embodiments of the present invention, similar principles and effects are applicable to liquid-sparged embodiments. Of course, the amount of gas and/or forth core can be decreased or absent altogether, however, the swirl flow of liquid carrier can be maintained. For example, in some high temperature applications, e.g., certain oxidation reactions, gaseous phases can be produced which would tend to migrate toward the center of the swirl flow. Further, the lower pressure present at the center of the swirl flow can allow dissolved gases to be liberated. Thus, it should be understood that the principles described herein and/or applied to an SG-SCR can also be applied to an SL-SCR.

The specific operating conditions can vary, depending on the desired reaction. However, the cyclone reactor can typically operate at reaction temperatures in the range of −20-350° C. and pressure range of 1-100 atm. Further, the cyclone reactor can operate over a wide range of temperature and pressure. The materials and thickness of the reactor can be adjusted in order to accommodate high reaction temperatures and pressures. For example, the thickness of the reactor body can be increased or decreased to account for varying reactor conditions. The reactor body can be formed of any material which is non-reactive with the liquid and gas compositions and is capable of withstanding the operating conditions such as temperature, pressure, abrasiveness and the like. Non-limiting examples of suitable materials includes stainless steel, INCONEL (Ni—Cr—Fe alloys), ceramic, plastics, and composites or alloys thereof.

In the most general form of the cyclone reactor, a liquid carrier including a liquid and an optional catalyst can be provided. In one embodiment, the liquid carrier can comprise homogenous solid catalyst particles (e.g., 1-10 µm) suspended or dissolved in a liquid such as an oil phase. The catalyst particles can be provided in a variety of forms such as, but not limited to, powder, particulate, needles, coated surfaces, coated particles, or the like. In another embodiment, the liquid carrier can comprise a liquid catalyst (e.g. $H_2SO_4$ and/or HF, depending on the specific reaction). The liquid carrier can be fed tangentially through a cyclone header into a porous tube to develop a swirl flow of a certain thickness in the radial direction. Depending on the synthesis process and reaction kinetics a plurality of gas-sparged catalytic cyclone reactors can be oriented in series and/or parallel to achieve a desired conversion, yield, and/or reaction sequence.

In the case of exothermic reactions (synthesis gas processes, alkylation, etc.), the process temperature can be determined either by controlling the inlet temperature of the liquid carrier and reaction substrates, vaporizing lower boiling liquid products into the gas phase, and/or inserting a cooling coil into the reaction space of the cyclone reactor. Generally, cooling elements can be placed in thermal contact with the liquid carrier in the swirl flow and/or the reactor body. For example, cooling coils can be placed inside the reactor body within the swirl flow. Preferably, the cooling coils can be oriented to minimize flow disturbance, e.g. parallel to flow direction. Alternatively, or in addition to internal cooling coils, a cooling jacket or cooling coils can be placed around the outside of the reactor body. In an arrangement of SG-SCRs working in series, the cooling units can be placed between the reactors or along feed lines to each reactor.

Exceptional dispersion of the reactant compositions with the liquid phase enhances, among other things, robust reaction conditions, reduces consumption of catalyst and, in some cases, suppresses unwanted side reactions. Due to improved mass and heat transfer characteristics, and high throughput per unit reactor volume, use of this reactor is expected to enable significant reductions in capital and operational costs of synthesis gas processes relative to either multi-tubular or gas-sparged reactors. The SG-SCR provides for the liquid carrier to pass through the reactor in essentially a rotating thin film. In sharp contrast to a conventional slurry reactor, the SG-SCR enables the liquid carrier to contact fresh reactants at every point along the reaction path. Thus, the liquid carrier primarily contacts unreacted reactants throughout the swirl flow and limits exposure of reaction products to the catalyst mixture. This assists in selective conversion of reactants to the desired products and reduces undesirable side reactions by reducing contact times. Further, the cyclone reactors of the present invention can allow for reduced reactor volumes due to improved contact between reactants and catalyst material and increased volume flow.

Another advantage for this system is the inherent decrease in erosion expected when using a catalyst slurry versus one where the catalyst slurry is in contact with metal surfaces at high velocity. In one embodiment of this system, the liquid carrier can ride on a cushion of reactant gas as it rotates in cyclone swirl flow through the reactor, very rarely touching the interior surfaces of the reactor body in normal operation. One of the more difficult problems encountered with liquids containing solids, such as in coal and shale upgrading is erosion of those parts of the equipment subjected to high velocity slurry flow.

Special design considerations can be used to establish the conditions necessary for high efficiency reactions. Some of these considerations are discussed in more detail below.

Principles of Operation

Some of the factors which can be used to describe the fluid flow phenomena within the present invention are swirl layer thickness, residence time, velocity of swirl layer and gas bubble size distribution. The experimental results showing that the swirl-layer thickness is independent of the fluid flow-rate and cylinder length, and can range from about 3% to about 15%, and often approximately 10% of the radius of the cyclone reactor. This condition was established from experiment and/or theory. For example, the calculated values of the swirl layer thickness using Taylor's inviscid theory for swirl nozzles are 0.103R or 2.5 mm for 51 mm tube and 0.08R or 4.1 mm for 102 mm tube.

The cyclone reactor can be sized to almost any capacity, depending on the intended application without affecting the basic function of the reactor. However, most often the cyclone reactor can have a reactor body having an inner diameter from about 4 cm to about 1 meter and preferably from about 5 cm to about 0.5 meter. The discussion herein focuses on a cylindrical reactor body; however, other configurations can also be used. For example, the reactor body can have a conical shape on at least the interior surface. In this example, the conical shape can narrow in diameter toward the outlet. In this way, flow velocities and local pressures can be controlled and maintained at predetermined levels without additional devices.

Experimental results indicate a swirl layer thickness that can vary from 1.9 mm to 3.1 mm for 51 mm diameter tube. Residence times of fluid forming the swirl layer have been calculated from experimental data and are typically 0.2-0.3 sec for a liquid phase creating a swirl layer. Generally, the residence time of gas bubbles $t_b$ can be calculated from Equation 1.

$$t_b = \frac{18\eta(1 + 0.15\text{Re}_g^{0.687})\delta}{a_{cen}d_b^2(\rho_s - \rho_g)} \quad (1)$$

where $\eta$ is the dynamic viscosity of a liquid phase, $\text{Re}_g$ is the Reynolds number for feed gas bubbles, $\delta$ is the thickness of a swirl layer, $a_{cen}$ is the centrifugal acceleration, $d_b$ is the diameter of a feed gas bubble, $\rho_s$ is the density of a liquid phase, and $\rho_g$ is the density of a gas phase feed.

Bubble size of the dispersed gas phase in a moving liquid is a critical factor which controls the rate and efficiency of reactions. It can be estimated from Equation 2.

$$d_b = \frac{4}{u}\left[\frac{r_c \cdot \sigma \cdot \eta^2}{f^2 \cdot \xi \cdot \rho_s^3}\right]^{\frac{1}{4}} \quad (2)$$

where $r_c$ is the capillary radius, $\sigma$ is the interfacial liquid-gas tension, u is the liquid phase velocity, f is the friction factor, and $\xi$ is the drag coefficient.

For high volumetric flow of a naphtha liquid phase, naptha droplets tends to form chains, and Equation 3 should be used.

$$d_b = \sqrt{\frac{3 \cdot Q_g}{\pi \cdot u}} \quad (3)$$

where $Q_g$ is the volumetric flow rate of a gas phase.

For cyclone reactors having a uniform cross-section along the length of the reactor body, a loss of angular momentum of the swirl layer occurs and the velocity of the liquid phase changes with the length of reactor. In this regard, the liquid velocity is the highest at the top of reactor and much lower at the bottom. The change in velocity influences gas bubble size according to above equations. The velocity of a liquid phase at definite point of reactor can be estimated from Equation 4.

$$u = \frac{u_{in}}{1 + \frac{\pi \cdot f \cdot R \cdot u_{in}}{Q_n}x} \quad (4)$$

where $u_{in}$ is the inlet velocity of liquid, R is the radius of reactor, and x is the distance from the inlet of liquid to the reactor.

Examples of Potential Applications

The cyclone reactors of the present invention can be used in a wide variety of chemical synthesis processes. Suitable processes can include, but are not limited to, synthesis gas processes (e.g. methanol, dimethyl ether, Fischer-Tropsch, and higher alcohols syntheses); partial oxidation of organic compounds; hydrocarbon conversions (e.g. hydroprocessing of heavy oils, bio-oils, tar sands, coal-derived liquids and shale oil, alkylation, and olefin oligomerization); and other processes with gas, liquids, and/or solids slurries, or processes with gases and two liquid phases. The liquid carrier can be any fluid capable of establishing the desired swirl flow, and in some cases, capable of suspending catalyst particles therein.

1. Synthesis Gas Processes

In these example processes, synthesis gas (typically a mixture of $H_2$ and CO, although other gases can be present), can be sparged through the jacketed porous tube wall where it is sheared into numerous small bubbles by the high-velocity swirl flow of the catalyst slurry at the inner surface of the porous tube. This results in the outstanding dispersion of synthesis gas feed and excellent contact with the catalyst suspended in oil. Due to centrifugal force and buoyancy, the gas bubbles accelerate toward the inner surface of the swirl layer resulting in separation of the low-density gas bubbles from the high-density slurry. In one embodiment of the present invention, the solid catalyst-oil slurry and product containing the slurry flow can be discharged through the annular opening created between the tube wall and a valve which is located on the cylindrical axis at the bottom of the reactor. In another embodiment, a liquid phase catalyst can be used in an analogous process. In both embodiments, the gas overflow can be discharged through either the top or bottom of the reactor. The liquid carrier, catalyst, reaction product and/or unreacted gas can also be discharged through the valves located on the cylindrical axis at the bottom of the reactor, although other discharge configurations can be used.

By way of example, methanol can be produced from synthesis gas using catalysts such as Cu/ZnO, Cu/ZnO/$Al_2O_3$, Cu/ZnO/MnO, RANEY Cu—Al—Zn, RANEY Cu—$Al_2$, Th$Cu_x$, and Zr$Cu_x$. Typical reaction conditions for methanol synthesis are temperatures from about 180° C. to about 250° C. and pressures from about 40 atm to about 150 atm. Non-limiting examples of suitable liquid carriers include mineral oils such as fully saturated paraffin oils (e.g., $C_{12}$-$C_{50}$), and the like.

In another example, dimethyl ether can be produced from synthesis gas using catalysts such as Co-catalyst systems composed of methanol synthesis catalysts (see above) and dehydration catalysts (e.g., HZSM-5, acidic alumina, $SiO_2$—$Al_2O_3$). Typical reaction conditions for dimethyl ether synthesis are temperatures from about 220° C. to about 340° C. and pressures from about 40 atm to about 150 atm. Non-limiting examples of suitable liquid carriers include mineral oils such as fully saturated paraffin oils (e.g., $C_{12}$-$C_{50}$), and the like.

In yet another process example, various hydrocarbons can be produced via Fischer-Tropsch processes. In order to produce lower alkanes ($C_2$-$C_4$), catalysts such as Fe/K, Fe/Mn, Fe/Mn/Ce, Fe/K/S, Ru/$TiO_2$, Fe/C, Mo/C, and the like can be used. Gasolines can be produced using catalyst such as fused Fe/K, Co/$ThO_2$/$Al_2O_3$/silicalite, Fe/K/ZSM-5, Co-ZSM-5, Ru-ZSM-5, Ru/ZSM-5, FeCu/K-ZSM-5, and the like. Diesel fuels can be formed using catalysts such as Fe/K, Ru/V/$TiO_2$, Co/Zr, Ti/$Al_2O_3$, Cr/$Al_2O_3$, Co/Zr/$TiO_2$, Co—Ru/$Al_2O_3$, and the like. Heavier waxes can be formed using catalysts such as Fe/Cu/K, Fe/R, Co/Zr, Ti/$Al_2O_3$ or Cr/$Al_2O_3$. Typical reaction conditions for Fischer-Tropsch synthesis are temperatures from about 180° C. to about 350° C. and pressures from about 20 atm to about 50 atm. Non-limiting examples of suitable liquid carriers include paraffin oils (e.g., $C_{12}$-$C_{50}$), heavy oily Fischer-Tropsch products, or the like.

Higher alcohols can be synthesized from synthesis gas using catalysts such as K—$MoS_2$, K—Co—$MoS_2$, Cs—$MoS_2$, K—Zn—Cr, K—Cu—Zn—Al, K—Cu—Co—Al, and Cs—Cu—ZnO—$Cr_2O_3$. Typical reaction conditions for higher alcohol synthesis can be temperatures from about 250° C. to about 425° C. and pressures from about 20 atm to about 200 atm. Non-limiting examples of suitable liquid carriers include mineral oils such as fully saturated paraffin oils (e.g., $C_{12}$-$C_{50}$), and the like.

2. Partial Oxidation of Organic Compounds

A mixture of $O_2$ (or air), optionally with a hydrocarbon reactant, can be used in the present invention for the oxidation of a variety of organic compounds. Non-limiting examples of suitable liquid carriers include paraffin oils (e.g., $C_{12}$-$C_{50}$), water, liquid reactant, and the like. When using water as a liquid carrier, typically lower temperatures are preferred in order to reduce decomposition and/or inactivation of the catalyst material. The following lists identify several suitable oxidations reactions and associated potential catalyst materials and reaction conditions.

(a) Methanol to formaldehyde

Catalysts:

High purity silver powder, $Fe_2O_3$/$Cr_2O_3$/$MoO_3$
Reaction Conditions:

Temperature: 300-700° C.
Pressure: ambient (b) Ethylene to ethylene oxide

Catalysts: Ag/α-$Al_2O_3$
Reaction Conditions:

Temperature: 200-250° C.
Pressure: 10-30 atm (c) Propylene to acrolein/acrylic acid Catalysts: $BiO_2$—$Mo_2O_3$
Reaction Conditions:

Temperature: 320-430° C.
Pressure: ambient (d) Ammoxidation of propylene to acrylonitrile Catalysts: $Bi_2O_3$—$MoO_3$/$SiO_2$
Reaction Conditions:

Temperature: 450-600° C.
Pressure: 1-3 atm (e) n-Butane to maleic anhydride

Catalysts: Vanadium-phosphorus-containing (VPO) catalyst, VPO/$TiO_2$,
Reaction Conditions:

Temperature: 360-400° C.
Pressure: 1-3 atm (f) Ethylene to vinyl acetate

Catalysts: Pd/$SiO_2$, $PdCl_2$/$CuCl_2$
Reaction Conditions:

Temperature: 100-200° C.
Pressure: 1-30 atm

3. Hydrocarbon Conversions

The following hydrocarbon conversion processes represents a broad variety of possible synthesis reactions which are suitable for use in the present invention.

(a) Aliphatic Alkylation with Solid Catalysts

In this example, a solid acid catalyst can be suspended in a liquid carrier and fed into the porous tube of the reactor. Non-limiting examples of suitable liquid carriers include fully saturated paraffin oils (e.g., $C_{12}$-$C_{50}$) and the like. Gaseous reactants, such as olefins and isobutane, are sparged through the jacketed porous tube wall and sheared into numerous small bubbles by the high-velocity swirl flow of the oil-catalyst slurry, at the inner surface of the porous tube. The catalyst slurry, reaction product and unreacted gas are discharged through the valves located on the cylindrical axis at the bottom of the reactor.

Catalysts: Potential solid acid catalysts for this process are exchanged zeolites, ion-exchange resins (e.g., AMBERLYST and NAFION), superacid solids (e.g., chlorinated alumina and sulfated zirconia), immobilized superacids (e.g., HF—$SbF_5$/$Al_2O_3$, $BF_3$/zeolites or oxides or resins), and heteropolyacid-based catalysts.

| Reaction Conditions: | |
|---|---|
| Temperature: | −20-30° C. |
| Pressure: | ambient |

(b) Olefin Oligomerization

In this example, a solid catalyst suspended in a liquid carrier can be fed into the porous tube of the reactor and gaseous olefins are sparged through the gas-sparging device and sheared into numerous small bubbles by the high-velocity swirl flow of the liquid carrier, at the inner surface of the porous tube. Non-limiting examples of suitable liquid carriers include paraffin oils (e.g., $C_{12}$-$C_{50}$), liquid reactants, and the like.

Catalysts: Phosphoric acid on a solid support (e.g., quartz and kieselguhr) or amorphous or crystallizes (zeolites) silica-aluminas.

| Reaction Conditions: | |
|---|---|
| Temperature: | 100-200° C. |
| Pressure: | 5-50 atm |

(c) Hydrogenation

In this example $H_2$ can be sparged through the gas-sparging device and is sheared into numerous small bubbles by the high-velocity swirl flow of the liquid carrier. Non-limiting examples of suitable liquid carriers include paraffin oils (e.g., $C_{12}$-$C_{50}$), liquid hydrogenation products (e.g., recycled products), and the like.

Catalysts: Precious metals such as Pd, Pt, Rh, and Ru unsupported and supported (e.g., Pt/C, Pd/$Al_2O_3$), and Ni, Cu, Cr and Co and their oxides (e.g., Raney Ni, Ni/$Al_2O_3$, and CuO—$Cr_2O_3$)

| Reaction Conditions: | |
|---|---|
| Temperature: | 20-350° C. |
| Pressure: | 1-0 atm |

(d) Hydrocracking

In the hydrocracking example, a liquid carrier such as vacuum distillate, deasphalted residues, gas oil, kerosene, etc., can be fed to the reactor together with suspended finely divided catalyst particles. Hydrogen can be used as the reactant gas that is sparged through the porous layer. The catalyst slurry, reaction product and unreacted gas are discharged through the valves located on the cylindrical axis at the bottom of the reactor.

Catalysts: CoMo/$SiO_2$—$Al_2O_3$, NiW/$SiO_2$—$Al_2O_3$, CoMo/$Al_2O_3$ (acid treated), NiW/$Al_2O_3$ (acid treated), Pt/zeolite, and Pd/zeolite.

| Reaction Conditions: | |
|---|---|
| Temperature: | 290-525° C. |
| Hydrogen partial pressure: | 50-200 atm |

(e) Hydrotreating

Any and all reactions that are generally termed hydrotreating in the petroleum refining industry can be accomplished in the cyclone reactor systems of the present invention. For example, heavy oil, or any petroleum derived oil as well as tar sand, bitumen, shale oil, coal liquids or bio-oils, that needs to be upgraded can be fed to the reactor as the liquid carrier, together with suspended finely divided catalyst particles. Hydrogen can be used as the reactant gas that is sparged through the porous tube in order to effect such reactions as hydrodesulfurization, hydrodenitrogenation, hydrodeoxygenation, hydrocracking, and the like.

Catalysts: CoMo/$Al_2O_3$, NiMo/$Al_2O_3$, NiW/$Al_2O_3$, and CoMo/$Al_2O_3$

| Reaction conditions for light petroleum distillate: | |
|---|---|
| Temperature: | 300-400° C. |
| Hydrogen partial pressure: | 15-60 atm |
| Reaction conditions for heavy petroleum residues, bio-oils, tar sands, coal-derived liquids and shale oil: | |
| Temperature: | 300-425° C. |
| Hydrogen partial pressure: | 50-150 atm |

4. Reactions Involving a Liquid Catalyst Phase

A wide variety of reactions can involve liquid catalyst phases. Typically, liquid catalyst phases can be provided as a liquid phase catalyst or as a homogeneous catalyst dissolved in a liquid carrier. Liquid phase catalysts can include, but is not limited to, sulfuric acid, fluoric acid, or the like. Non-limiting examples of reactions which can benefit from the use of liquid phase catalysts can include aliphatic alkylation (as described above), synthesis of napthenic kerosene, and other known reactions.

Frequently, a homogenous catalyst can be dissolved in a liquid carrier and/or formed as a metal complex which can be dispersed in the liquid carrier. For example, $AlCl_3$ based homogeneous catalysts can be useful in many synthesis reactions such as, but not limited to alkylation reactions. Generally, homogeneous catalysts comprising transition metal complexes can be useful in a variety of reactions such as, but not limited to, carbon-hydrogen bond formation, e.g., hydrogenation and related processes, carbon-carbon bond formation, e.g., oligomerization and polymerization, reactions with carbon monoxide, oxygen transfer reactions, chiral catalysis, or the like.

Those skilled in the art will recognize that the above processes are merely guidelines and conditions and materials can vary from those listed. The following literature can be used as background in designing specific synthesis processes and additional considerations in operation of the present invention, each of which are incorporated herein by reference: Olah, G. A., "The Methanol Economy," Chemical & Engineering News, 81(38), 2003; Miller J. D., "Air-sparged Hydrocyclone and Methods", U.S. Pat. No. 4,279,743 (1981); Miller J. D., and Kinneberg D. J., "Fast Flotation with an Air-sparged Hydrocyclone", Proc. of MINTEK 50, Int. Confer. on Recent Advances in Mineral Science and Technology, Johannesburg, South Africa, March 1984, 373-383; Mills, G. A., "Status and Future Opportunities for Conversion of Synthesis Gas to Liquid Fuels", Fuel, 1994, 73(8), 1243-1279; and Grisham et. al., "Method and Apparatus for Optimizing and Controlling Gas-Liquid Phase Chemical Reactions," U.S. Pat. No. 5,730,875 (1998).

Thus, there is disclosed an improved reactor and methods for preparing chemical compounds. The above description and examples are intended only to illustrate certain potential embodiments of this invention. It will be readily understood by those skilled in the art that the present invention is susceptible to a broad utility and applications. Many embodiments and adaptations of the present invention other than those herein described, as well as many variations, modifications and equivalent arrangements will be apparent from or reasonably suggested by the present invention and the foregoing description thereof without departing from the substance or scope of the present invention. Accordingly, while the present invention has been described herein in detail in relation to its preferred embodiment, it is to be understood that this disclosure is only illustrative and exemplary of the present invention and is made merely for purpose of providing a full and enabling disclosure of the invention. The foregoing disclosure is not intended or to be construed to limit the present invention or otherwise to exclude any such other embodiment, adaptations, variations, modifications and equivalent arrangements, the present invention being limited only by the claims appended hereto and the equivalents thereof.

What is claimed is:

1. A method of reacting compounds, comprising the steps of:
   a) passing a liquid catalyst mixture through a flow-through interior chamber of a reactor;
   b) forming a swirl layer of the liquid catalyst mixture; and
   c) injecting a reactant composition including a reactant through at least a portion of the swirl layer such that at least a portion of the reactant is converted to a reaction product.

2. The method of claim 1, wherein the reactant composition is a gas composition containing at least one gaseous reactant.

3. The method of claim 1, wherein the reactant is a cylindrical gas-sparged cyclone.

4. The method of claim 3, wherein the step of injecting the gas composition includes forcing the gas composition across a porous layer configured to sparge the gas composition and increase surface area of the gas composition.

5. The method of claim 1, wherein the catalyst mixture has a flowrate which is adjusted to achieve a predetermined swirl layer thickness and residence time.

6. The method of claim 2, further comprising the step of removing liquid and gas phases independently from the reactor.

7. The method of claim 1, wherein the step of forming the swirl layer creates a vortex induced pressure differential sufficient to increase transfer of reactants across the swirl layer.

8. The method of claim 5, wherein the swirl layer has a thickness from about 5% to about 20% of a diameter of the interior chamber.

9. The method of claim 1, further comprising removing heat from the swirl layer.

10. The method of claim 1, wherein the catalyst mixture contains a solid catalyst to provide a catalyst slurry.

11. The method of claim 1, wherein the catalyst mixture contains a liquid catalyst.

12. The method of claim 1, wherein the reactant composition comprises a plurality of gaseous reactants.

13. The method of claim 10, further comprising the step of recycling the catalyst slurry.

14. The method of claim 1, further comprising the step of recovering the reaction product.

15. The method of any of claims 1, 10, or 11, wherein the catalyst mixture comprises a liquid carrier selected from the group consisting of mineral oil, paraffin oil, heavy fractions of the reaction product, water, liquid reactant, and mixtures thereof.

16. The method of claim 1, wherein the reactant composition comprises a gas selected from the group consisting of hydrogen and carbon monoxide, oxygen, oxygen and gaseous reactant, hydrogen, and gaseous reactant.

17. The method of claim 1, wherein the reaction product is selected from the group consisting of methanol, dimethyl ether, Fischer-Tropsch products, higher alcohols, oxidation products, oligomerization products, hydrogenation products, hydrotreated hydrocarbons.

18. The method of claim 10, wherein the catalyst slurry comprises at least one methanol synthesis catalyst.

19. The method of claim 10, wherein the catalyst slurry comprises methanol synthesis catalyst and dehydration catalyst.

20. The method of claim 12, wherein the reactant composition comprises synthesis gas.

21. The method of claim 11, wherein the reactant composition is synthesis gas and the reaction product is methanol.

22. The method of claim 18, wherein the reactant composition is synthesis gas and the reaction product is dimethyl ether.

* * * * *